United States Patent
Wood et al.

(10) Patent No.: US 6,803,227 B2
(45) Date of Patent: Oct. 12, 2004

(54) ORGAN PRESERVATION SYSTEM INCLUDING ARTICLES COMPRISING A SUPER-COOLABLE COMPOSITION HAVING LONG-DURATION PHASE CHANGE CAPABILITY

(75) Inventors: Brian Wood, Lubbock, TX (US); Allan J. Cassell, Melbourne (AU)

(73) Assignee: Supachill Technologies Pty. Ltd., West Heidelberg (AU)

( * ) Notice: Subject to any disclaimer, the term of this patent is extended or adjusted under 35 U.S.C. 154(b) by 119 days.

(21) Appl. No.: 09/978,837

(22) Filed: Oct. 16, 2001

(65) Prior Publication Data

US 2003/0073226 A1 Apr. 17, 2003

(51) Int. Cl.⁷ .................................................. A01N 1/02
(52) U.S. Cl. .................................. 435/284.1; 435/303.1
(58) Field of Search ............................... 252/70.67, 71; 435/1.2, 1.3, 284.1, 303.1; 62/114, 371, 434, 457.2, 457.9

(56) References Cited

U.S. PATENT DOCUMENTS

| | | | | |
|---|---|---|---|---|
| 3,995,444 A | * | 12/1976 | Clark et al. | 62/306 |
| 4,322,954 A | * | 4/1982 | Sheehan et al. | 62/371 |
| 5,157,930 A | * | 10/1992 | McGhee et al. | 62/78 |
| 5,285,657 A | | 2/1994 | Bacchi et al. | 62/457.9 |
| 5,326,706 A | * | 7/1994 | Yland et al. | 435/1.2 |

OTHER PUBLICATIONS

Supercooling. Wikipedia online encyclopedia. [online], [retrieved on Feb. 24, 2004]. Retrieved from the internet <URL:http://en.wikipedia.org/wiki/superco>.*

* cited by examiner

Primary Examiner—William H. Beisner
(74) Attorney, Agent, or Firm—Raymond M. Galasso; Simon, Galasso & Frantz PLC

(57) ABSTRACT

An organ preservation system according to one embodiment of the disclosures herein includes a perfusion liquid delivery apparatus, a perfusion liquid pumping apparatus and a thermal mass. The perfusion liquid pumping apparatus is connected to the perfusion liquid delivery apparatus and is capable of delivering a perfusion liquid to the perfusion liquid delivery apparatus. The thermal mass includes a thermal mass cooling core body having a core cavity therein. A cooling member is disposed in the core cavity of the thermal mass cooling core body. A super-coolable composition is disposed within the core cavity of the thermal mass cooling core body encapsulating at least a portion of the cooling member. The cooling member is coupled between the perfusion liquid delivery apparatus and the perfusion liquid pumping apparatus and is capable of having the perfusion liquid routed therethrough for enabling the perfusion liquid to be cooled.

23 Claims, 13 Drawing Sheets

ORGAN PRESERVATION SYSTEM INCLUDING ARTICLES COMPRISING A SUPER-COOLABLE COMPOSITION HAVING LONG-DURATION PHASE CHANGE CAPABILITY

FIELD OF THE DISCLOSURE

The disclosures herein relate generally to organ preservation systems and more particularly to an organ preservation system including articles comprising a super-coolable composition having long-duration phase change capability.

BACKGROUND OF THE DISCLOSURE

It is common for a donor organ for a transplant procedure to be removed from a donor at one facility and to be transported to another facility where a transplant recipient is awaiting the transplant procedure. Often, such facilities are at distant locations relative to each other. To minimize degradation of the donor organ during transportation, the donor organ is generally transported using an organ transportation apparatus that maintains the organ in a chilled state and that provides for perfusion of an oxygenated and nutrient-balanced solution (hereinafter referred to as the perfusion liquid) through vessels and/or cavities of the donor organ.

Maintaining the donor organ in the chilled state provides several advantages relative to the viability of the donor organ in the transplant procedure. One advantage is that maintaining the donor organ in the chilled state lowers the metabolic activity of the donor organ's, thus reducing the demand for physiologic oxygen levels and consumption of nutrients. Another advantage is that by assisting in lowering the metabolic activity of the donor organ's cells, the rate of production of by-products of metabolism such as carbon dioxide and lactic acid is reduced, thus reducing tissue damage and stabilizing the pH level and osmotic balance of the perfusion liquid. Yet another advantage is that the demand for oxygen in reduces, thus protecting against inadequate oxygen levels that can result in ischemic tissue.

To maintain the donor organ in the chilled state, it is common for the donor organ to be contained in an insulated organ container, for the perfusion liquid to be chilled and/or for the entire organ preservation system to be contained in an insulated organ preservation system container. The insulated organ container and the insulated organ preservation system container include provisions for maintaining the donor organ contained therein in the chilled state for a period of time. Chilling of the perfusion liquid is accomplished by a number of techniques, including circulating the perfusion liquid through a heat exchanging device and providing a reservoir of chilled perfusion liquid in an insulated container.

Passive-type insulated containers include insulating material for reducing the rate of heat transfer between contents therein and an ambient environment. Other than such insulating material, no other means is provided for maintaining an item contained therein in a particular thermal condition. Active-type insulated containers include insulating material and a climate preservation implement. The climate preservation implement is capable of actively maintaining a volume of the container at a particular thermal condition. Powered cooling devices and conventional thermal masses (e.g. freezable cold packs, ice blocks, etc.) are examples of climate preservation implements.

Conventional insulated containers, thermal masses and techniques for cooling the perfusion liquid suffer from several limitations that impair their ability to maintain the donor organ in the chilled state for an extended period of time (e.g. as long as 50 hours) during transport. Examples of such limitations include a limited time duration that conventional thermal masses can maintain a frozen/chilled state, the degree of super-cooling achievable by conventional thermal masses, the effectiveness of conventional passive-type insulated containers, the limited time a portable power supply can sustain the operation of a powered cooling device and the operating efficiency, weight and space associated with such powered cooling device.

In many ways, these limitations have a significant adverse affect on organ transplant procedures and organ donation in general. Examples of such adverse affects include impairing the physiological condition of a donor organ, limiting the selection of donor organs to a particular organ recipient, limiting the scheduling predictability for surgical teams and limiting the feasibility of a world-wide network of organ donors and organ recipients. Accordingly, an organ preservation system that at least partially overcomes limitations associated with maintaining a profusion fluid and a donor organ in a desired chilled state during transport of the donor organ is useful.

DETAILED DESCRIPTION

Figure 1:
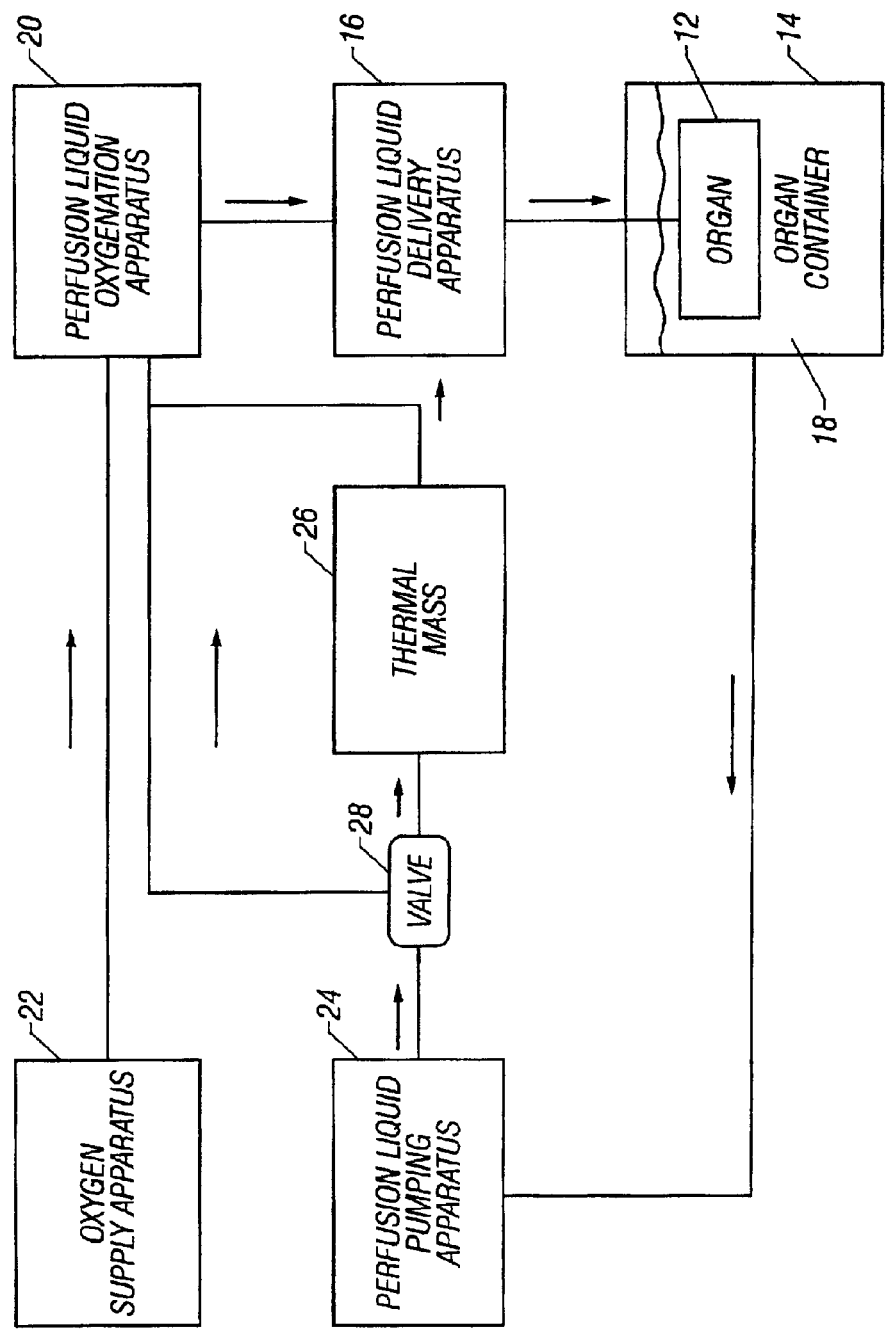
FIG. 1 is a block diagram view depicting an organ preservation system in accordance with an embodiment of the disclosures made herein.

FIGS. 1 through 18 depict, in accordance with various embodiments of the disclosures made herein, an organ preservation system including articles comprising a super-coolable composition having long-duration phase change capability, a process for preparation of such super-coolable composition and a process of super-cooling such super-coolable composition. Embodiments of the super-coolable composition disclosed herein provide advantageous capabilities and characteristics. Specifically, such super-coolable composition exhibits a very long-duration capability and returns to a pre-frozen gel consistency after being super-cooled and thawed. Such embodiments of the super-coolable materials are formulated to suit the specific requirements and/or application and, then after being super-cooled, have been exhibited to maintain a desired below freezing temperature for as long as 50 hours. Accordingly, an organ preservation system in accordance with an embodiment of the disclosures herein is capable of maintaining a donor organ in a desired chilled state for a considerably longer period of time than a conventional organ FIG. 1 depicts an organ preservation system 10 in accordance with an embodiment of the disclosures herein. The organ preservation system 10 is a self-contained system capable of maintaining a donor organ 12 as a viable organ for a transplant procedure during transport of the donor organ 12. For example, the organ preservation system 10 is capable of transporting the donor organ 12 from a first facility where the donor organ 12 has been removed from an organ donor entity to a second facility where the donor organ 12 will be implanted in or otherwise physiologically associated with an organ recipient.

Figure 2:
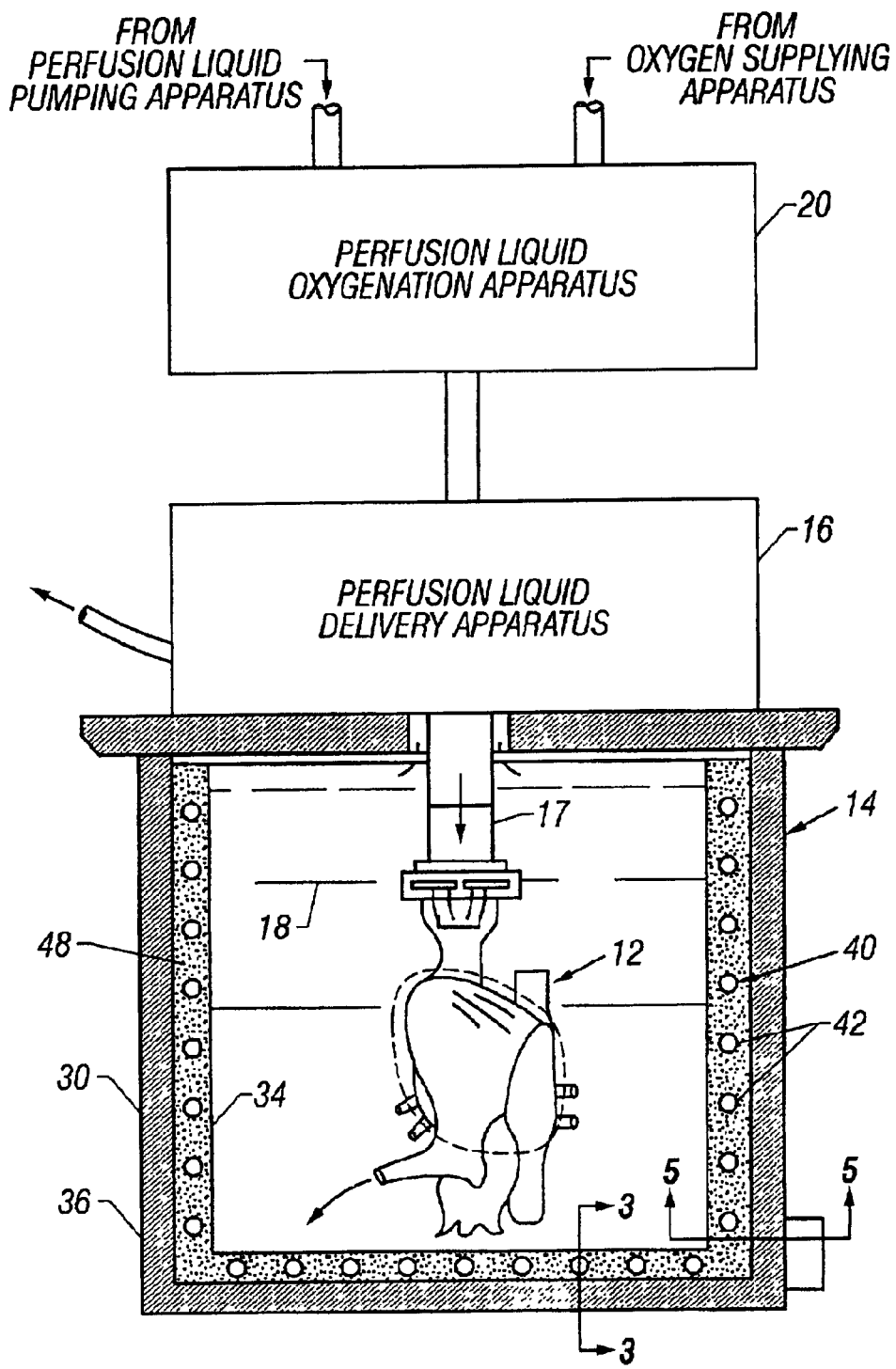
FIG. 2 is a partial cross-sectional view depicting an organ storage container in accordance with an embodiment of the disclosures made herein.

Referring to FIGS. 1 and 2, the donor organ 12 is stored in an organ container 14 and is attached to a fluid dispensing device 17 of a liquid delivery apparatus 16. The organ container 14 serves as a perfusion liquid reservoir at least partially filled with a perfusion liquid 18. The donor organ 12 is immersed within the perfusion liquid 18 within the organ container 14. The perfusion liquid delivery apparatus 16 facilitates perfusion of the perfusion liquid 18 through vessels and cavities of the donor organ 12. In one embodiment of the perfusion liquid 18, the perfusion liquid 18 is a nutrient-balanced solution capable of providing nourishment to the donor organ 12.

The perfusion liquid delivery apparatus 16 is connected to a perfusion liquid oxygenating apparatus 24 via a supply conduit. An oxygen supplying apparatus 26 and the perfusion liquid pumping apparatus 20 are connected to the perfusion liquid oxygenating apparatus 24. The perfusion liquid oxygenating apparatus 24 facilitates oxygenation of the perfusion liquid as supplied by the perfusion liquid pumping apparatus 20. The perfusion liquid pumping apparatus 20 operates to receive the perfusion liquid 18 from the organ container 14 via a return conduit and to pump the perfusion liquid 18 for being received by the perfusion liquid delivery apparatus 16 via the perfusion liquid oxygenating apparatus 24. The thermal mass 22 is connected between the perfusion liquid oxygenating apparatus 24 and the perfusion liquid pumping apparatus 20. In this manner the perfusion liquid delivery apparatus 16 is capable of delivering to the donor organ 12 the perfusion liquid 18 in an oxygenated and chilled state. Oxygenation of a perfusion liquid, such as the perfusion liquid 18, is known to advantageously affect the effectiveness of an organ preservation system, such as the organ preservation system 10.

As disclosed herein and discussed below in greater detail in reference to FIGS. 6 through 9, the thermal mass 22 includes a super-coolable composition therein and a cooling member encapsulated within the super-coolable composition. Also disclosed herein and discussed below in greater detail in reference to FIGS. 17 and 18, the cooling member 40 is capable of being connected to a cooling apparatus for having a super-cooled cooling fluid circulated therethrough. In this manner, the super-coolable composition of the thermal mass 22 is capable of being super-cooled.

After the super-coolable composition of the thermal mass 22 is super-cooled, connection of the thermal mass 22 within the organ preservation system 10 allows for the perfusion liquid 18 to be cooled by the thermal mass 22. The super-coolable composition of the thermal mass 22 advantageously permits cooling of the perfusion liquid 18 for as long as 50 hours or more.

In practice, organs are often pre-chilled (i.e. thermally equalized) to a desired preservation temperature prior to being removed from a host body. For example, it is preferred to pre-chill a human heart to between about 2 degrees Celsius and about 6 degrees Celsius prior to removing the heart from a human body. By pre-chilling the organ to the desired preservation temperature prior to removal from the host body, an organ preservation system has the task of maintaining the organ at the pre-chilled temperature rather than reducing the organ from a body temperature to a desired chilled preservation temperature.

The embodiment of the organ preservation apparatus 10 depicted in reference to FIG. 1A does not include an active element (such as a temperature sensitive valve) for dynamically maintaining the temperature of the perfusion liquid 18 within a desired temperature range. Accordingly, heat generating components within the system such as heat added to the perfusion liquid 18 by the perfusion liquid pumping apparatus 20 and heat associated with metabolism of the organ are used for determining a degree of super-cooling of the thermal mass 22 suitable for maintaining the temperature of the perfusion liquid 18 within a desired temperature range. A preferred temperature range for perfusion liquid flowing through a human heart is between about 2 degrees Celsius and about 6 degrees Celsius.

The organ preservation system 10, in accordance with another embodiment of the disclosures herein (not shown), does not include an active element (such as a temperature sensitive valve) for dynamically maintaining the temperature of the perfusion liquid 18 within a desired temperature range. Accordingly, heat generating components within the system such as heat added to the perfusion liquid 18 by the perfusion liquid pumping apparatus 20 and heat associated with metabolism of the organ are used for determining a degree of super-cooling of the thermal mass 22 suitable for maintaining the temperature of the perfusion liquid 18 within a desired temperature range.

A valve 28 is connected between the perfusion liquid pumping apparatus 20. The valve 28 is capable of routing the flow of the perfusion liquid 18 through the thermal mass 22 or diverting the flow of the perfusion liquid 18 around the super-coolable thermal mass 22. The valve 28 directs the flow of the perfusion liquid, (i.e. through the super-coolable thermal mass 22 or diverted around the super-coolable thermal mass 22) according to the temperature of the perfusion liquid at a particular location in the organ preservation system 10. Examples of locations where the temperature of the perfusion liquid 18 is monitored for determining flow through the valve 28 include between the perfusion liquid delivery apparatus 16 and the organ container 14, between the organ container 14 and the perfusion liquid pumping apparatus 20 and at the valve 28. A preferred temperature range for perfusion liquid flowing through a human heart is between about 2 degrees Celsius and about 6 degrees Celsius.

Various devices and techniques for controlling the valve 28 are known in the art. One example of such devices and techniques includes a temperature sensor capable of providing a signal to a control motor (not shown) of the valve 28 for affecting the manner in which perfusion liquid 18 flows through the valve 28. Another example of such devices and techniques includes a thermostat mechanically coupled to the valve 28 for affecting the manner in which the perfusion liquid 18 flows through the valve 28.

Although the super-coolable thermal mass 22 is depicted at a particular respective location in FIG. 1, it is contemplated herein that the super-coolable thermal mass 22 may be positioned at other locations in the organ preservation system 10. In one example of an alternate position, the super-coolable thermal mass 22 is positioned between the valve 28 and the organ container 14. In another example of an alternate position, the super-coolable thermal mass 22 is positioned between the perfusion liquid oxygenating apparatus 20 and the perfusion liquid delivery apparatus 16.

The various functional components of the organ preservation system 10 may be functionally and structurally integrated, physically integrated and functionally separate or physically and functionally separate. In one example, the perfusion liquid oxygenating apparatus 20 is functionally and structurally integrated with the perfusion liquid delivery apparatus 16. In another example, the perfusion liquid delivery apparatus 16 and the organ container 14 are structurally integrated. In yet another example, the control valve 28 is structurally and functionally integrated with the perfusion liquid pumping apparatus 20. Various types of and arrangements for perfusion liquid oxygenating apparatuses, oxygen supplying apparatuses, perfusion liquid oxygenation apparatuses, perfusion liquid delivery apparatuses and donor organ containers are known in the art.

Figure 3:
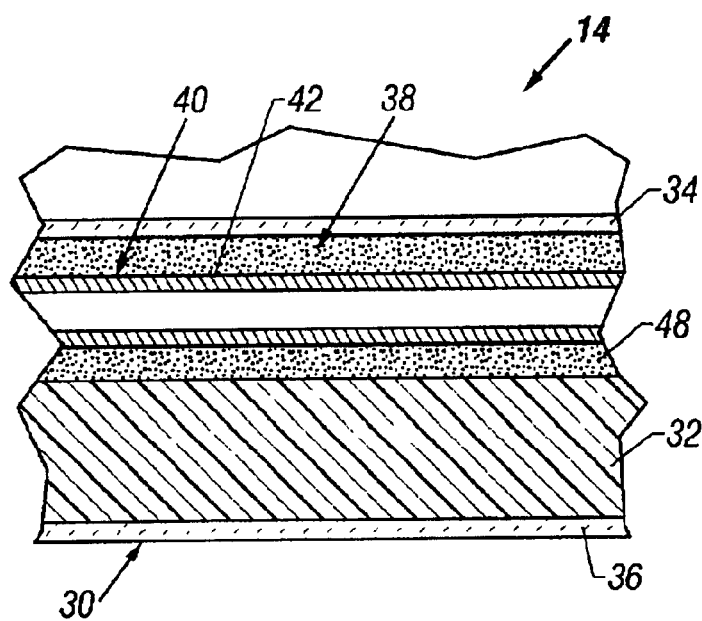
FIG. 3 is a cross-sectional view taken along the line 3—3 in FIG. 2.
Figure 4:
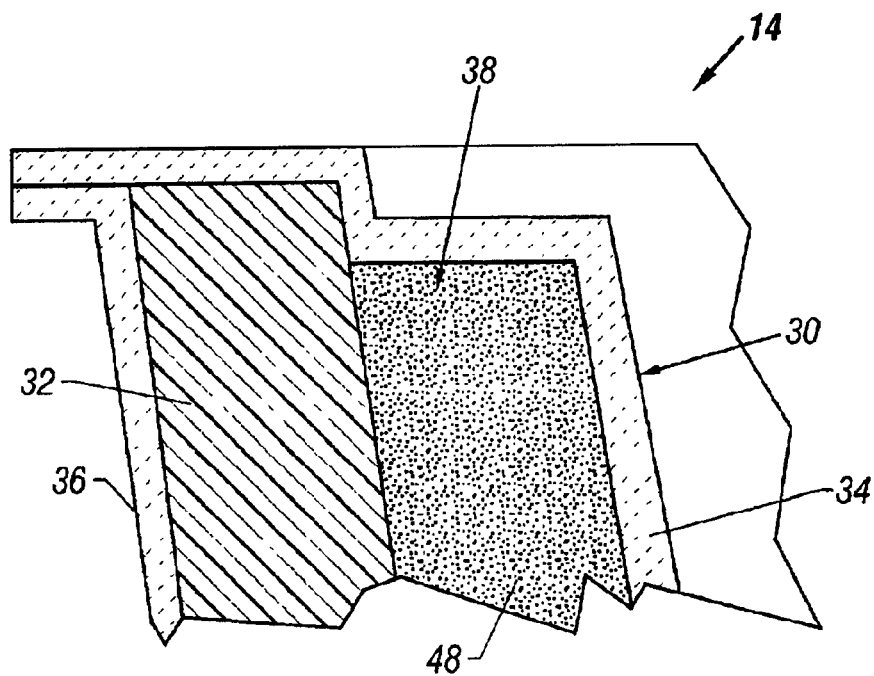
FIG. 4 is an enlarged cross-sectional view taken at the location designated view 4 in FIG. 2.
Figure 5:
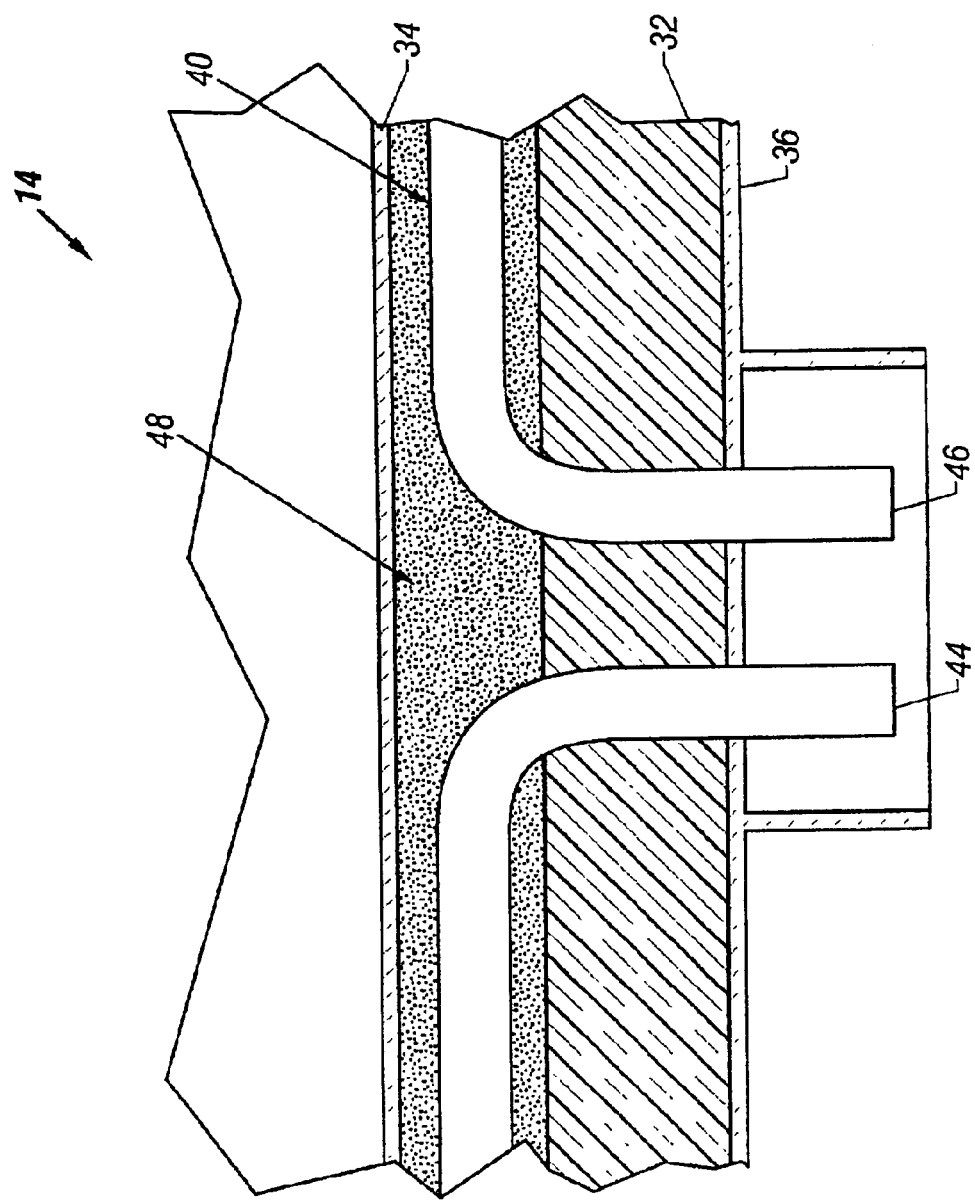
FIG. 5 is a cross-sectional view taken along the line 5—5 in FIG. 2.

Referring to FIGS. 2 through 4, the organ container 14 includes an internally-insulated cooling core assembly 30. The cooling core assembly 30 includes an insulating insert 32, a first cooling core shell 34 and a second cooling core shell 36. The first cooling core shell 34 and the second cooling core shell 36 are joined along mating edges using a known technique such as laser welding, ultrasonic welding, solvent cement or the like, thus forming an organ container cooling core body.

A core cavity 38, FIGS. 3 and 4, is defined within the organ container cooling core body. The term internally-insulated as used herein refers to insulation being provided internal to the core cavity 38. Accordingly, the insulating insert 32 is disposed within the organ container cooling core body between the first cooling core shell 34 and the second cooling core shell 36 prior to attaching the first cooling core shell 34 to the second cooling core shell 36. It is contemplated herein that the insulating insert 32 may consist of one or more pieces. Although the organ container 14 is depicted and disclosed herein as having an internally-insulated cooling core assembly, it is contemplated herein that the cooling core assembly of the organ container 14 may have an externally-insulated cooling core assembly of essentially the same construction as the system container 102 of the system container assembly 100 disclosed below in reference to FIGS. 11 through 14.

In one embodiment of the first cooling core shell 34 and the second cooling core shell 36, the first cooling core shell 34 and the second cooling core shell 36 are made of polyethylene and are capable of being made using a known technique such as injection molding, rotational molding or blow molding. It is contemplated herein that the first cooling core shell 34 and the second cooling core shell 36 may be independently formed, or jointly formed and subsequently separated as needed.

The insulating shell 32 may be attached to or in detached engagement with the second cooling core shell 36. Polystyrene foam and polyethylene foam are examples of material from which the insulating insert 32 may be made. It is contemplated herein that the insulating shell 32 may be made from flexible materials, compliant materials, rigid materials or a combination thereof.

The cooling core assembly 30 includes a cooling member 40 disposed within the core cavity 38 of the cooling core assembly 30. The cooling member 40 includes a plurality of spaced cooling member segments 42, a first cooling member coupling 44 and a second cooling member coupling 46. The first cooling member coupling 44 and the second cooling member coupling 46 extend through the second cooling core shell 36 and the insulating insert 32. The cooling member 40 is configured such that the plurality of spaced cooling member segments 42 are essentially evenly spaced throughout the core cavity 38. It is contemplated herein that the cooling member 40 may be alternatively configured that the spaced cooling member segments 42 are unevenly spaced.

It is contemplated herein that the cooling member 40 may be fabricated according to a variety of construction arrangements. In one construction arrangement, the cooling member 40 is made from a length of conformable material such as copper or polymeric tube that is bend into a single-pass configuration having a plurality of loops (e.g. back and forth loops). Each loop of such a single-pass configuration defines one of the spaced cooling member segments 42. The single-pass configuration results in a serial flow of a cooling fluid through each one of the spaced cooling member segments. In another construction arrangement, the cooling member 42 has a multi-pass configuration. In such multi-pass configuration, the spaced cooling member segments 42 are connected in a manner that allows a cooling fluid, such as disclosed below in reference to FIGS. 17 and 18, to travel through multiple paths. For example, connecting a plurality of discrete pieces of cooling member segments (straight or having bends) between a first cooling fluid manifold and a second cooling fluid manifold provides such a multi-pass coil configuration.

A cooling coil having plurality of s-shaped coils and a cooling coil having a helical wound configuration are examples of cooling members and/or cooling member segments disclosed herein. It is contemplated herein that cooling members disclosed may be made of metal, polymeric materials, ceramic materials and the like.

Figure 16:
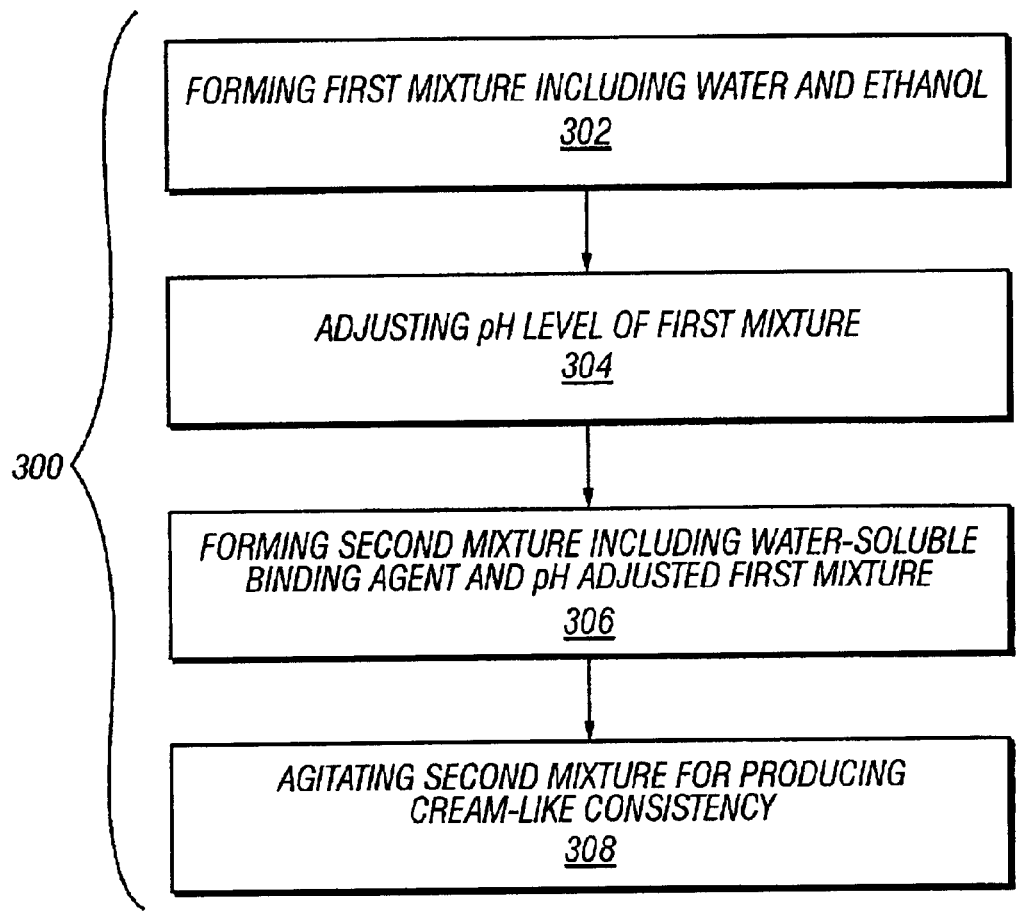
FIG. 16 is a flow chart view depicting a process for preparation of a super-coolable composition in accordance with an embodiment of the disclosures made herein.

At least a portion of the core cavity 38 not occupied by the cooling member 40 or the insulating insert 32 is filled with a super-coolable composition 48, such as the super-coolable composition as disclosed herein in reference to FIG. 16. The spaced cooling member segments 42 of the cooling member 40 are essentially encapsulated in the super-coolable composition 48. The first cooling member coupling 44 and the second cooling member coupling 46 provide a means for connecting a cooling apparatus to the cooling member 40. As discussed below in reference to FIGS. 17 and 18 in greater detail, the cooling member 40 is capable of being connected to a cooling apparatus. The cooling apparatus is capable of circulating a super-cooled cooling fluid through the cooling member 40 for super-cooling the super-coolable composition 48. Accordingly, the cooling member 42 facilitates an initial super-cooling operation for taking the super-coolable composition 48 to a super-cooled state. The cooling member 42 also enables subsequent super-cooling operations for 'recharging' the super-coolable composition 48 to the super-cooled state after the super-coolable composition 48 has fully or partially thawed.

Figure 6:
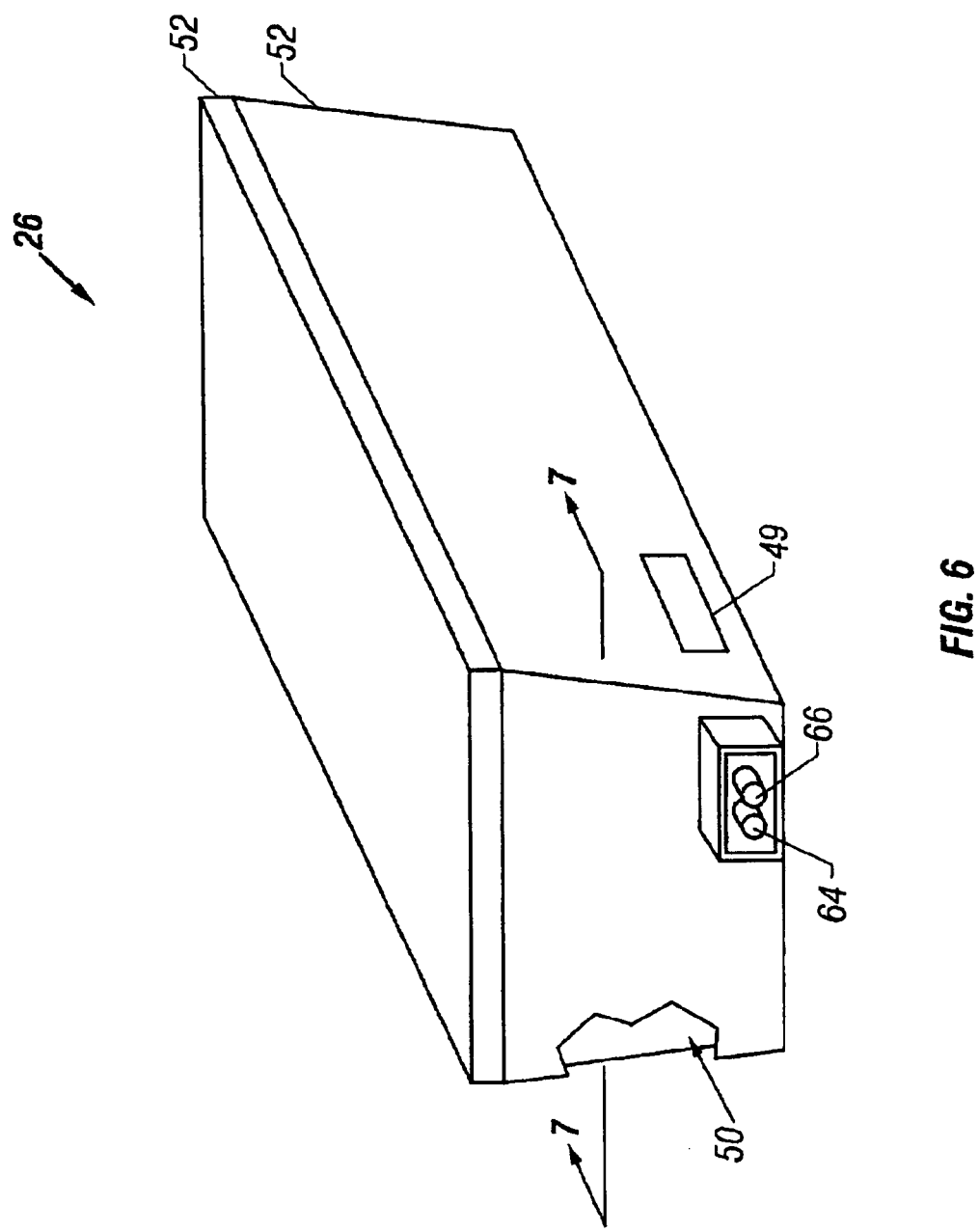
FIG. 6 is a perspective view depicting a thermal mass according to an embodiment of the disclosures herein, wherein the thermal mass includes an externally-insulated cooling core assembly.
Figure 7:
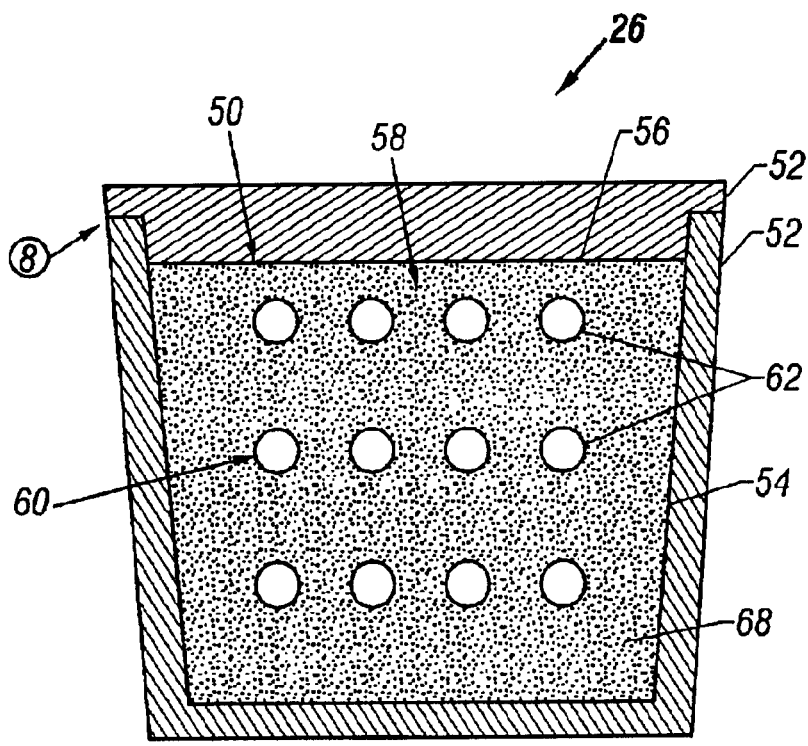
FIG. 7 is a cross-sectional view taken along the line 7—7 in FIG. 6.
Figure 8:
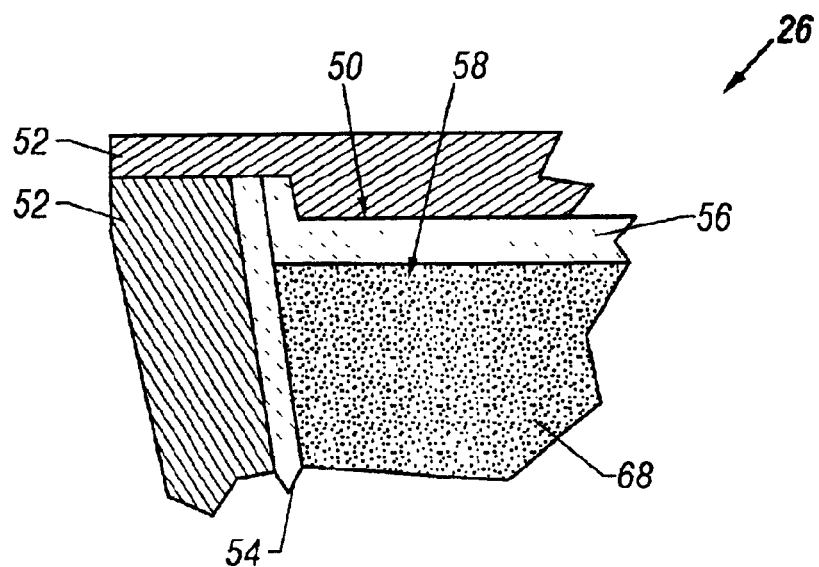
FIG. 8 is an enlarged cross-sectional view taken at the location designated view 8 in FIG. 7.

Various aspects of the thermal mass 22 are depicted in FIGS. 6 through 8. It should be understood that a thermal mass as disclosed herein, such as the thermal mass 22, is an embodiment of a cooling core assembly as disclosed herein. It is contemplated herein that a thermal mass, such as the thermal mass 22, may have a variety of shapes (e.g. rectangular, round, etc.) and may have different profiles (e.g. flat, cylindrical, etc.).

The thermal mass 22 includes an information storage device 49, FIG. 6. A commercially available radio frequency identification tags such as those offered by Texas Instruments Incorporated are examples of the information storage device 49. The information storage device 49 permits various information about the thermal mass 22 to be monitored. For example, information associated with shipping routes, time-to-delivery, ambient temperatures and detailed information about the apparatuses connected to the thermal mass 22 may be transmitted to and received from the information storage device 49.

Referring to FIGS. 7 and 8, the thermal mass 22 includes an externally-insulated cooling core assembly 50 and an insulating shell 52. The cooling core assembly 50 includes a first cooling core shell 54 and a second cooling core shell 56, FIGS. 7 and 8. The first cooling core shell 54 and the second cooling core shell 56 are joined along mating edges using a known technique such as laser welding, ultrasonic welding solvent cement or the like, thus forming a thermal mass cooling core body. A core cavity 58 is defined within the thermal mass cooling core body.

In one embodiment of the first cooling core shell 54 and the second cooling core shell 56, the first cooling core shell 54 and the second cooling core shell 56 are made of polyethylene and are capable of being made using a known technique such as injection molding, rotational molding or blow molding. It is contemplated herein that the first cooling core shell 54 and the second cooling core shell 56 may be independently formed, or jointly formed and subsequently cut apart.

The insulating shell 52 covers a substantial portion of the first cooling core shell 54 and the second cooling core shell 56. It is contemplated herein that the insulating shell 52 may consist of a first portion and a second portion that jointly cover a substantial portion of the first cooling core shell 54 and the second cooling core shell 56. It is contemplated herein that the insulating shell 52 may have a mono-layer construction (i.e. a single insulating layer) or a multi-layer construction. A layer capable of providing conductive insulating functionality, a layer capable of providing vapor permeation functionality and a layer capable of providing radiant insulating functionality are examples potential layers in a multi-layer construction. The insulating shell 52 may be attached to or detached from the thermal mass cooling core body.

Polystyrene foam and polyethylene foam are examples of material layers capable of providing conductive insulation. PolarTherm brand material offered by Polar Thermal Products LTD is an example of an insulating shell having a multi-layer construction. It is contemplated herein that the insulating shell 52 may each be made from flexible materials, compliant materials, rigid materials or a combination thereof.

The cooling core assembly 50 includes a cooling member 60 positioned within the core cavity 58. The cooling member 60 includes a plurality of spaced cooling member segments 62, a first cooling member coupling 64 and a second cooling member coupling 66. The first cooling member coupling 64 and the second cooling member coupling 66 extend through the second cooling core shell 56 and the insulating shell 52, FIG. 6. The cooling member 60 is configured such that the plurality of spaced cooling member segments 62 are essentially evenly spaced throughout the core cavity 58. It is contemplated herein that the cooling member 60 may have a single pass configuration or a multi-pass configuration, as discussed above in reference to FIGS. 2 through 5.

At least a portion of the core cavity 58 not occupied by the cooling member 60 is filled with a super-coolable composition 68, such as the super-coolable composition as disclosed herein in reference to FIG. 16. One embodiment of a technique for dispensing the super-coolable composition 68 into the core cavity 58 includes dispensing the super-coolable composition 68 through a suitable aperture (not shown) in the first cooling core shell 54 or second cooling core shell 56. The aperture is plugged or covered after the super-coolable composition 68 is dispensed into the cooling cavity 58. Another embodiment of a technique for dispensing the super-coolable composition 68 into the core cavity 58 includes dispensing the super-coolable composition 68 into the first cooling core shell 54 prior to attaching the second cooling core shell 56 to the first cooling core shell 54.

The spaced cooling member segments 62 of the cooling member 60 are essentially encapsulated in the super-coolable composition 68. As mentioned above, the first cooling member coupling 64 and the second coil 66 coupling provide a means for connecting a cooling apparatus to the cooling member 60. As discussed below in reference to FIGS. 17 and 18 in greater detail, the cooling apparatus is capable of circulating a super-cooled cooling fluid through the cooling member 60 for super-cooling the super-coolable composition 68.

Figure 9:
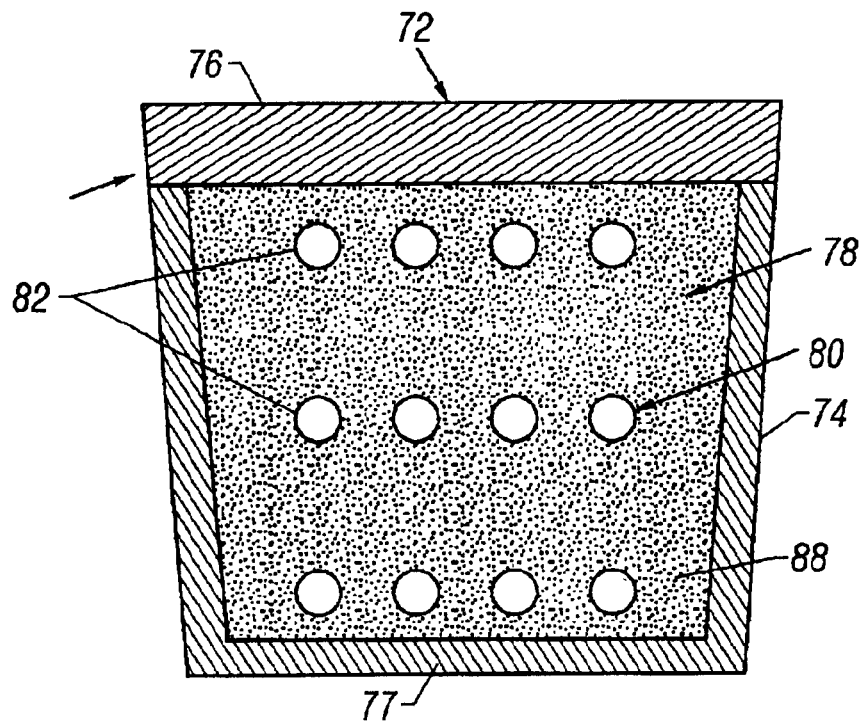
FIG. 9 is a cross sectional view depicting a thermal mass according to an embodiment of the disclosures herein, wherein the thermal mass includes an internally-insulated cooling core assembly.
Figure 10:
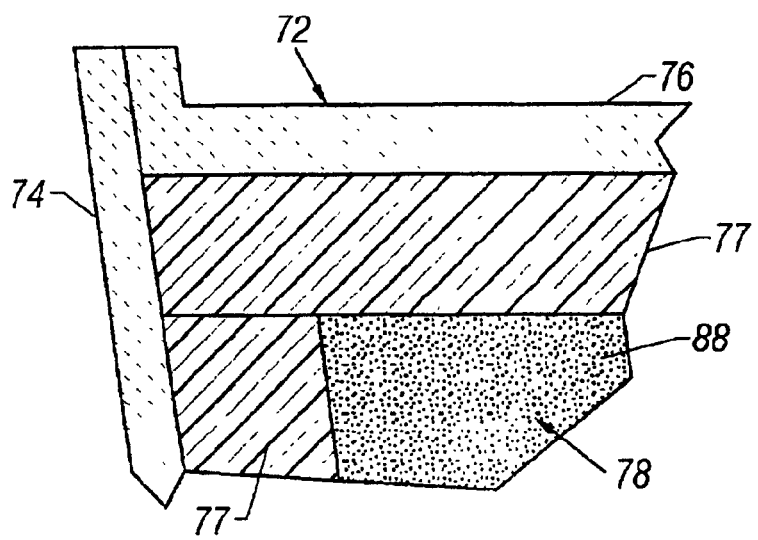
FIG. 10 is an enlarged fragmentary cross-sectional view taken at the location designated view 10 in FIG. 9.

A thermal mass 70 according to another embodiment of the disclosures herein is disclosed in reference to FIGS. 9 and 10. From a functional standpoint, the thermal mass 70 is essentially that same as the thermal mass 22 disclosed above in FIGS. 6 through 8. However, from a structural standpoint, the thermal mass 70 includes a number of differentiating aspects with respect to the thermal mass 22 disclosed above. Only those differentiating aspects will be described below.

The thermal mass 70 includes an internally-insulated cooling core assembly 72. The cooling core assembly 72 includes a first cooling core shell 74, a second cooling core shell 76 and an insulating insert 77. The first cooling core shell 74 and the second cooling core shell 76 are joined along mating edges using a known technique such as laser welding, ultrasonic welding solvent cement or the like, thus forming a thermal mass cooling core body. A core cavity 78 is defined within the thermal mass cooling core body. The insulating insert 77 is disposed within the core cavity 78 of the thermal mass cooling core body. It is contemplated herein that the insulating insert 77 may consist of one or more pieces.

A cooling member 80 is positioned within the core cavity 78. The cooling member 80 includes a plurality of spaced cooling member segments 82. At least a portion of the core cavity 78 not occupied by the cooling member 80 or the insulating insert 77 is filled with a super-coolable composition 88, such as the super-coolable composition as disclosed herein. The spaced cooling member segments 82 of the cooling member 80 are essentially encapsulated in the super-coolable composition 88. As discussed below in reference to FIGS. 17 and 18 in greater detail, a cooling apparatus is capable of circulating a super-cooled cooling fluid through the cooling member 80 for super-cooling the super-coolable composition 88.

Various aspects of a system container assembly 100 according to an embodiment of the disclosures herein are disclosed in reference to FIGS. 11 through 14. The system container assembly 100 includes a system container 102 and a container cover 104. The container cover 104 is capable of being moved between a first position P1 and a second position P2. A container cavity 106 of the system container 102 is accessible when the container cover 104 is in the first position P1 and is inaccessible when the container cover 104 is in the second position P2. A removable cover arrangement and a hinged cover arrangement are examples of arrangements for allowing the cover to be moved between the first position P1 and the second position P2.

Figure 11:
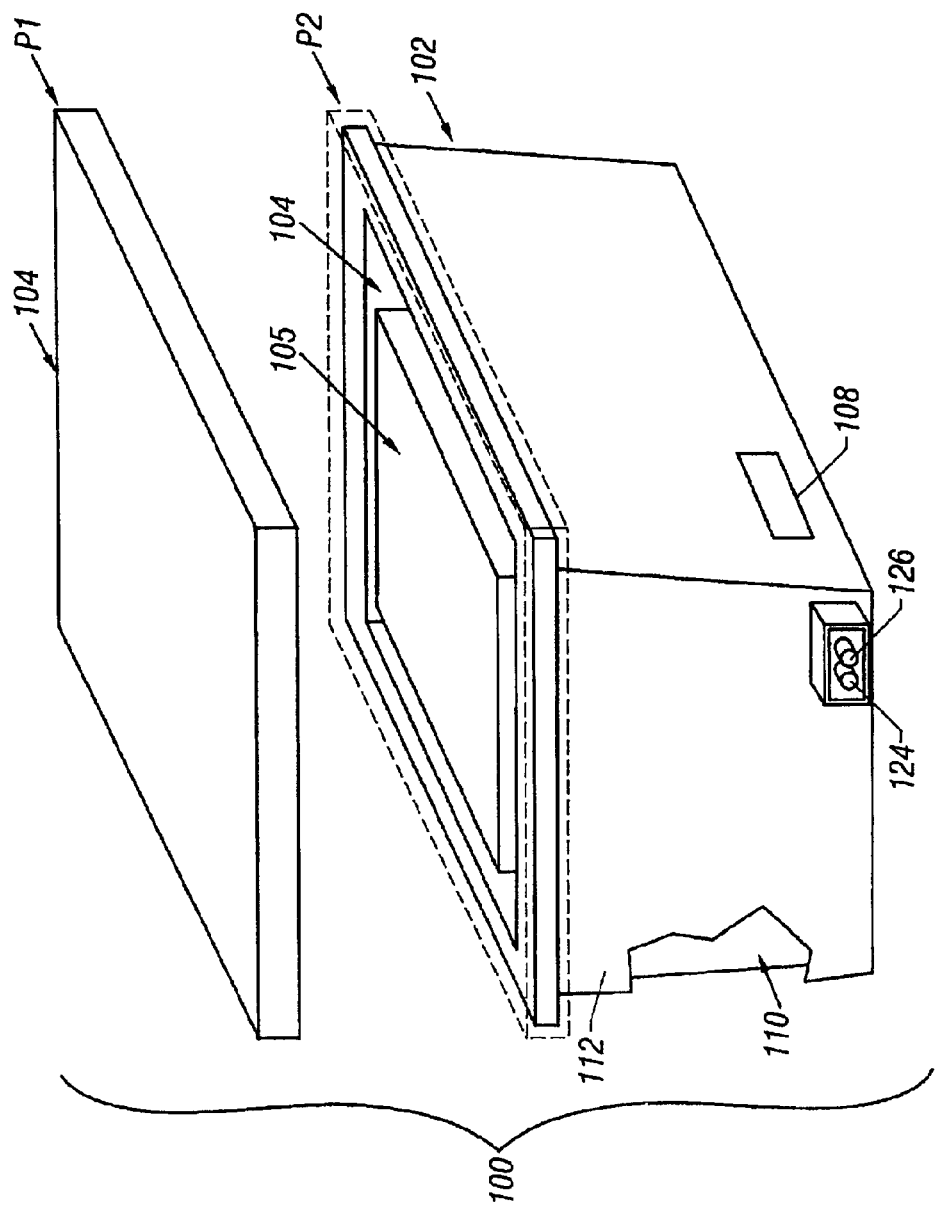
FIG. 11 is a partial cross-sectional view depicting an organ preservation system container in accordance with an embodiment of the disclosures made herein, wherein the organ preservation storage container has an externally-insulated cooling core assembly.
Figure 12:
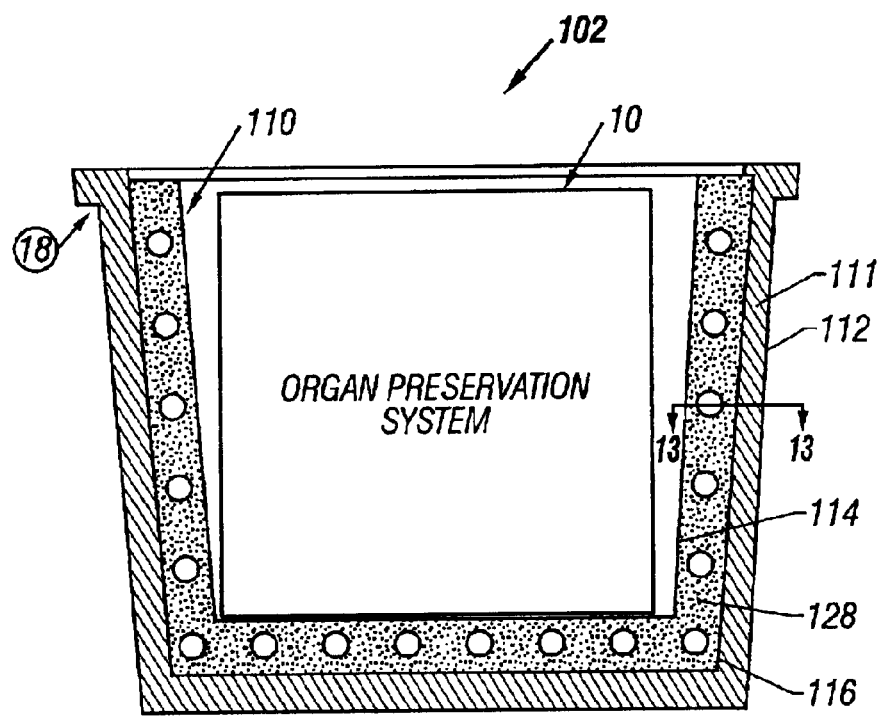
FIG. 12 is a cross-sectional view taken along the line 12—12 in FIG. 11.
Figure 13:
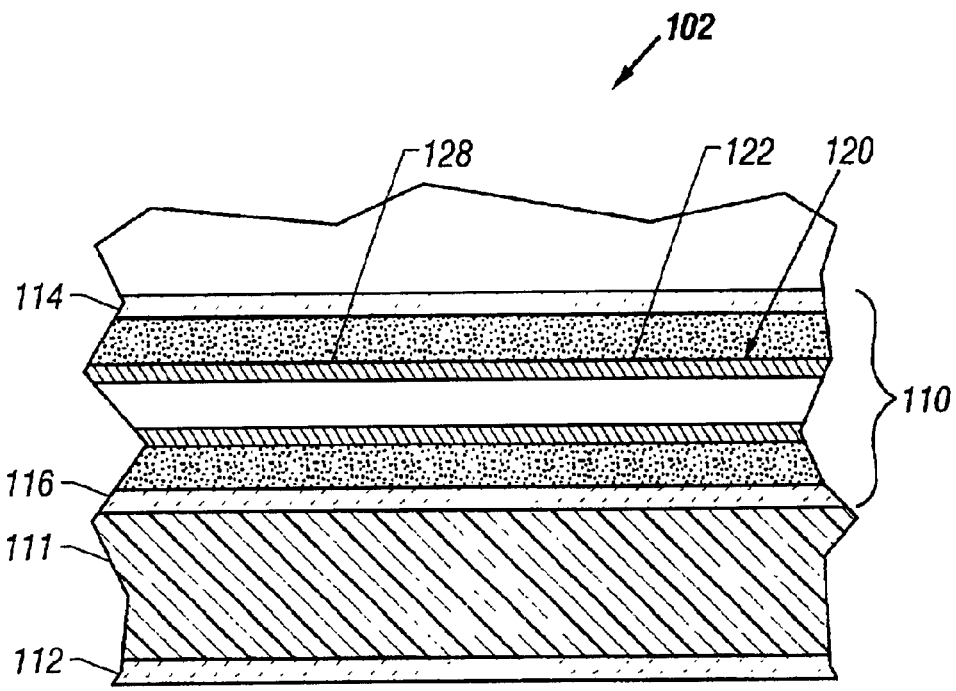
FIG. 13 is a cross-sectional view taken along the line 13—13 in FIG. 11.
Figure 14:
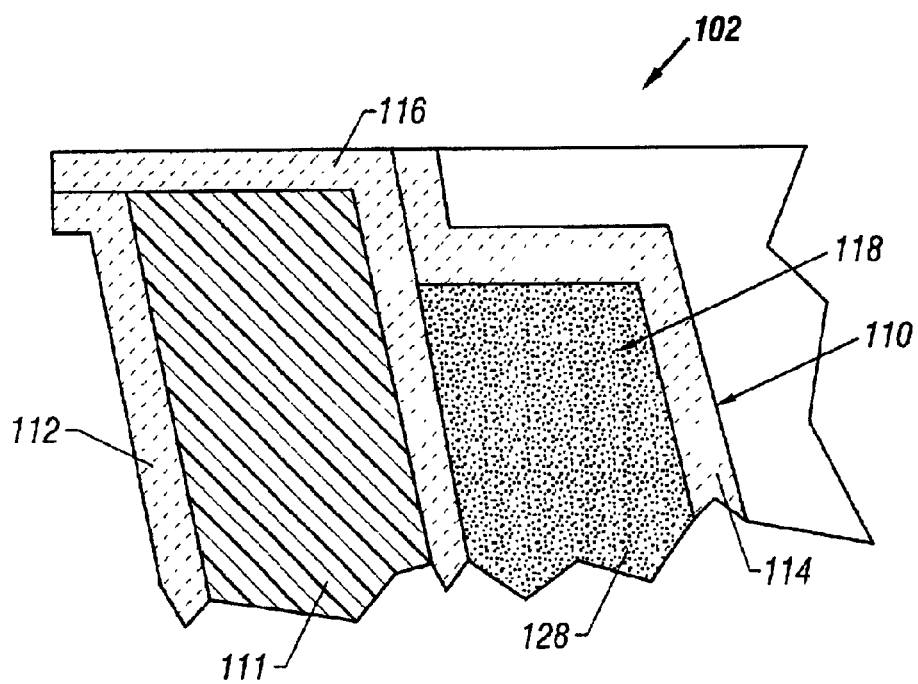
FIG. 14 is an enlarged fragmentary cross-sectional view taken at the location designated view 14 in FIG. 12.

As depicted in FIGS. 11 and 12, the system container 102 is capable of having the various apparatuses and ancillary components (a system assembly 105) of the organ preservation system 10, FIG. 1, contained within the container cavity 106. The system assembly 105 includes the thermal mass, the perfusion liquid delivery system, the perfusion liquid pumping system, and related apparatuses and components. It is contemplated herein that system assembly 105 is mountable on a carrier such as a tray or frame. In this manner, the carrier along with the system assembly 105 is capable of being placed in and removed from the container cavity 106 of the system container 102. As disclosed below, the construction and resulting functionality of the system container 102 contributes to maintaining a donor organ in a desired chilled state for a considerably longer period of time than a conventional organ preservations system.

The system container 102 includes an information storage device 108, FIG. 2, attached to the system container 102. It is contemplated herein that the information storage device 108 may be attached to the container cover 104 rather than to the system container 102. A commercially-available radio frequency identification tags such as those offered by Texas Instruments Incorporated is an example of the information storage device 108. The information storage device 108 permits various information about the system container 102 and contents of the system container 102 to be monitored. For example, information associated with shipping routes, time-to-delivery, ambient temperatures and detailed information about the contents of the system container 102 may be transmitted to and received from the information storage device 108.

The system container 102 includes an externally-insulated cooling core assembly 110, an insulating shell 111 and an exterior shell 112. One of the functions of the exterior shell 112 is to protect the insulating shell 111. The cooling core assembly 110 includes a first cooling core shell 114 and a second cooling core shell 116. The first cooling core shell 114 and the second cooling core shell 116 are joined along mating edges using a known technique such as laser welding, ultrasonic welding solvent cement or the like, thus forming a system container cooling core body. A core cavity 118 is defined within the system container cooling core body.

By externally-insulated, it is meant that insulation is provided external to the core cavity 118. Accordingly, the insulating shell 111 covers a substantial portion of the second cooling core shell 116. Although the system container 102 is depicted and disclosed as having an externally-insulated cooling core assembly, it is contemplated herein that the cooling core assembly 110 of the system container 102 may have an internally-insulated cooling core assembly of essentially the same construction as the cooling core assembly 30 of the organ container 14 disclosed above in reference to FIGS. 2 through 4.

In one embodiment of the first cooling core shell 114 and the second cooling core shell 116, the first cooling core shell 114 and the second cooling core shell 116 are made of polyethylene and are capable of being made using a known technique such as injection molding, rotational molding or blow molding. It is contemplated herein that the first cooling core shell 114 and the second cooling core shell 116 may be independently formed, or jointly formed and subsequently separated as needed.

It is contemplated herein that the insulating shell 111 may have a mono-layer (i.e. an insulating layer) construction or a multi-layer construction. A layer capable of providing conductive insulating functionality, a layer capable of providing vapor permeation functionality and a layer capable of providing radiant insulating functionality are examples potential layers in a multi-layer construction. The insulating shell 111 may be attached to or detached engagement with the cooling core assembly 110. Similarly, the insulating shell 111 may be attached to or detached engagement with the exterior shell 112.

Polystyrene foam and polyethylene foam are examples of material layers capable of providing conductive insulation. PolarTherm brand material offered by Polar Thermal Products LTD is an example of an insulating shell having a multi-layer construction. It is contemplated herein that the insulating shell 111 may be made from flexible materials, compliant materials, rigid materials or a combination thereof.

A cooling member 120 is positioned within the core cavity 118. The cooling member 120 includes a plurality of spaced cooling member segments 122, a first cooling member coupling 124 and a second cooling member coupling 126. The first cooling member coupling 124 and the second cooling member coupling 126 extend through the second cooling core shell 116, the insulating shell 111 and the exterior shell 112. The cooling member 120 is configured such that the plurality of spaced cooling member segments 122 are essentially evenly spaced throughout the core cavity 118 (i.e. present in each wall of cooling core assembly 110). It is contemplated herein that the cooling member 120 may be alternatively configured such that the spaced cooling member segments 122 are present in less than all of the walls of the cooling core assembly 110 and such that the spaced cooling member segments 122 are unevenly spaced.

It is contemplated herein that the cooling member may be fabricated according to a variety of construction arrangements. In one construction arrangement, the cooling member 120 is made from a length of conformable material such as copper or polymeric tube that is bend into a single-pass configuration having a plurality of loops (e.g. back and forth loops). Each loop of such a single-pass configuration defines one of the spaced cooling member segments 122. The single-pass configuration results in a serial flow of a cooling fluid through each one of the spaced cooling member segments. In another construction arrangement, the plurality of spaced cooling member segments 122 has a multi-pass coil configuration. In such another construction arrangement, the spaced cooling member segments 122 are connected in a manner allowing refrigerant to travel through multiple paths. For example, connecting a plurality of discrete pieces of cooling member segments (straight or having bends) between a first cooling fluid manifold and a second cooling fluid manifold provides such a multi-pass coil configuration.

A cooling coil having plurality of s-shaped coils and a cooling coil having a helical wound configuration are examples of cooling members disclosed herein. It is contemplated herein that cooling members disclosed may be made of metal, polymeric materials, ceramic materials and the like.

At least a portion of the core cavity 118 not occupied by the cooling member 120 is filled with a super-coolable composition 128, such as the super-coolable composition as disclosed herein. The super-coolable composition 128 is dispensed into the core cavity 118 through a suitable aperture (not shown). The aperture is plugged or covered after the super-coolable composition 128 is dispensed into the cooling cavity 118.

The spaced cooling member segments 122 of the cooling member 120 are essentially encapsulated in the super-coolable composition 128. The first cooling member coupling 124 and the second cooling member coupling 126 provide a means for connecting a cooling apparatus to the cooling member 120. As discussed below in reference to FIGS. 17 and 18 in greater detail, the cooling apparatus is capable of circulating a super-cooled cooling fluid through the cooling member 120 for super-cooling the super-coolable composition 128.

In one embodiment of the container cover 104, the container cover 104 consists of one or more layers of insulating material. In another one embodiment of the container cover 104, the container cover 104 includes a cooling core assembly with a cooling member and a super-coolable composition disposed within the cooling cavity. In such an embodiment of the container cover 104, it is contemplated herein that the cooling core assembly of the container cover 104 may have an internally-insulated configuration or an externally-insulated configuration, as disclosed herein.

Figure 15:
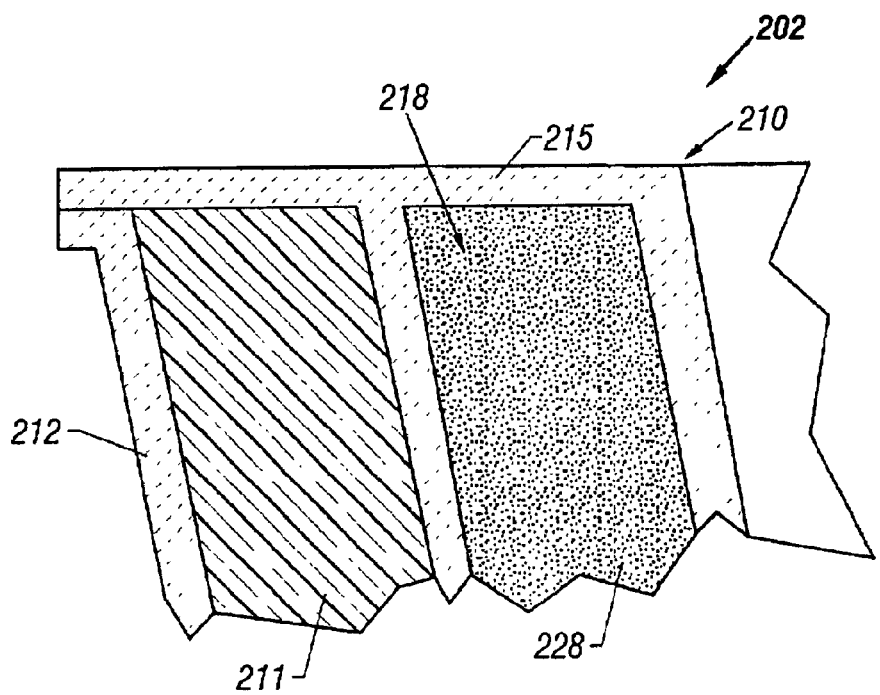
FIG. 15 is a cross-sectional view depicting an eternally-insulated cooling core assembly in accordance with an embodiment of the disclosures made herein, wherein the cooling core assembly has a unitary construction and omits a cooling member.

A container 202 according to another embodiment of the disclosures herein is disclosed in reference to FIG. 15. An organ container and a system container as disclosed herein are examples of applications for the container 202. The container 202 includes an externally-insulated cooling core assembly 210, an insulating shell 211 and an exterior shell 212. The cooling core assembly 210 includes a container cooling core body 215. The container cooling core body 215 has a core cavity 218 therein filled at least partially with a super-coolable composition 228. The cooling core body 215 and the exterior shell 212 are joined along mating edges using a known technique such as laser welding, ultrasonic welding solvent cement or the like.

The container cooling core body 215 has a unitary construction and is made by known techniques such as blow molding and rotational molding. The unitary construction of the cooling core body 215 precludes a cooling member from being disposed within the core cavity 218. Accordingly, the super-coolable composition 228 within the core cavity 218 is super-cooled by immersing the container body 202 in a tank of super-cooled cooling fluid. Such a tank of super-cooled cooling fluid is discussed below in reference to FIGS. 17 and 18 in greater detail.

It is contemplated herein that the thermal masses and containers disclosed herein are capable of being integrated into known and newly discovered organ preservation systems. Integration into some known organ preservation systems may or may not require substitution of an existing thermal mass, heat exchanger device, container or the like (e.g. a conventional organ container, a conventional thermal mass, a conventional heat exchanger or a conventional organ preservation system container.) Such substitution will be capable by one of ordinary skill in the related art. Examples of such known organ preservation systems are disclosed in U.S. Pat. Nos. 5,965,433; 5,362,622; 5,338,662; 5,326,706 and 5,285,657.

FIG. 16 depicts a process 300 for preparation of a super-coolable composition in accordance with another embodiment of the disclosures made. In the process 300, an operation 302 is performed for forming a first mixture including water and ethanol. Depending on the application, potable water may or may not be used. The ratios of water and ethanol will depend on the desired freezing point. Higher ratios of ethanol will generally translate to lower freezing temperatures. Stirring and blending water and Ethanol are examples of a technique for forming the first mixture.

After performing the operation 302 for forming the first mixture, an operation 304 is performed for adjusting the pH level of the first mixture. Accordingly, a pH adjusted first mixture is formed. Adding an alkaline or acidic substance to the first mixture is an example a technique for adjusting the pH level of the first mixture. Sodium bicarbonate is an example of a slightly alkaline substance. In one embodiment of the operation 302, adjusting the pH of the first mixture includes adjusting the pH level of the first mixture about 8.0.

After performing the operation 304 for adjusting the pH level of the first mixture, an operation 306 is performed for forming a second mixture including the pH adjusted first mixture and a binding agent. Stirring and blending the binding agent and the pH adjusted first mixture are examples of a technique for forming the second mixture. Cellulose Ester such as that offered by DOW Chemical Company under the tradename Methocel is an example of a commercially-available water-soluble binding agent. Methylcellulose and hydroxypropyl methylcellulose are examples of two different types of cellulose esters.

About 3% cellulose ester, by weight, is preferred for a mixture of about 30% ethanol to about 70% water. As little as 1% to 2% cellulose ester, by weight, is preferred as the percent of ethanol approaches zero. The PH level is preferably about 8 for the cellulose content disclosed above. However, it is contemplated and disclosed herein that the composition may have a pH level different than about 8 depending on the specific requirements of the composition. The importance of the pH being adjusted to a desired level is that by adjusting the PH level up or down influences the time frame in which the mix will gel.

After the operation 306 is performed for forming the second mixture, an operation 308 is performed for agitating the second mixture until the viscosity of the second mixture increases, thus providing the second mixture with a cream-like consistency. Stirring and blending are examples of agitating. The second mixture is a super-coolable composition including water, ethanol, a substance capable of adjusting the pH of a water and alcohol mixture to about 8, and water soluble binding agent.

EXAMPLE 1

Forming a Super-coolable Composition for Freezing at about −18 Degrees Celsius

Ethanol and potable water are blended at ratios of about 30% and about 70%, respectively, by weight, thus forming a first mixture. Sodium bicarbonate is then blended into the mixture of ethanol and water in a quantity sufficient to achieve a pH level of the mixture to about 8. Accordingly, a pH adjusted first mixture is formed. After forming the pH adjusted first mixture, Methocel brand cellulose ester is stirred in the pH adjusted first mixture at about 3% by weight to the mixture of water, ethanol and sodium bicarbonate, thus forming a second mixture. The second mixture is then stirred until a cream-like consistency is achieved. The second mixture is a super-coolable composition including water, ethanol, sodium bicarbonate and cellulose ester.

About 10 minutes after achieving the cream-like consistency, the second mixture begins to gel. Accordingly, within about 10 minutes of achieving the cream-like consistency, the second mixture is poured into an end use container.

It should be understood that the formulae for mixing super-coolable materials according to embodiments of the disclosures herein will vary depending on the phase change temperature desired and/or required. The example presented above represents only one of many examples of preparing a super-coolable material according to the disclosures herein.

The super-coolable compositions disclosed above in reference to FIG. 16 and Example 1 exhibit a long-duration phase change capability and returns to a pre-frozen gel consistency after being super-cooled and thawed. There is no separation of fluid layers upon super-cooling the composition to −18 degrees Celsius or more and once thawed. The lack of fluid layer separation is advantageous as solubilization of the composition in subsequent cooling cycles increases after a first cooling and thawing cycle. When a super-cooling operation is performed on the composition, a portion of the water in the composition is held in the latent heat super-cooled state and does not freeze. The heat normally released on freezing of the water (referred to as the heat of fusion) is decreased by the amount of super-cooling.

Figure 17:
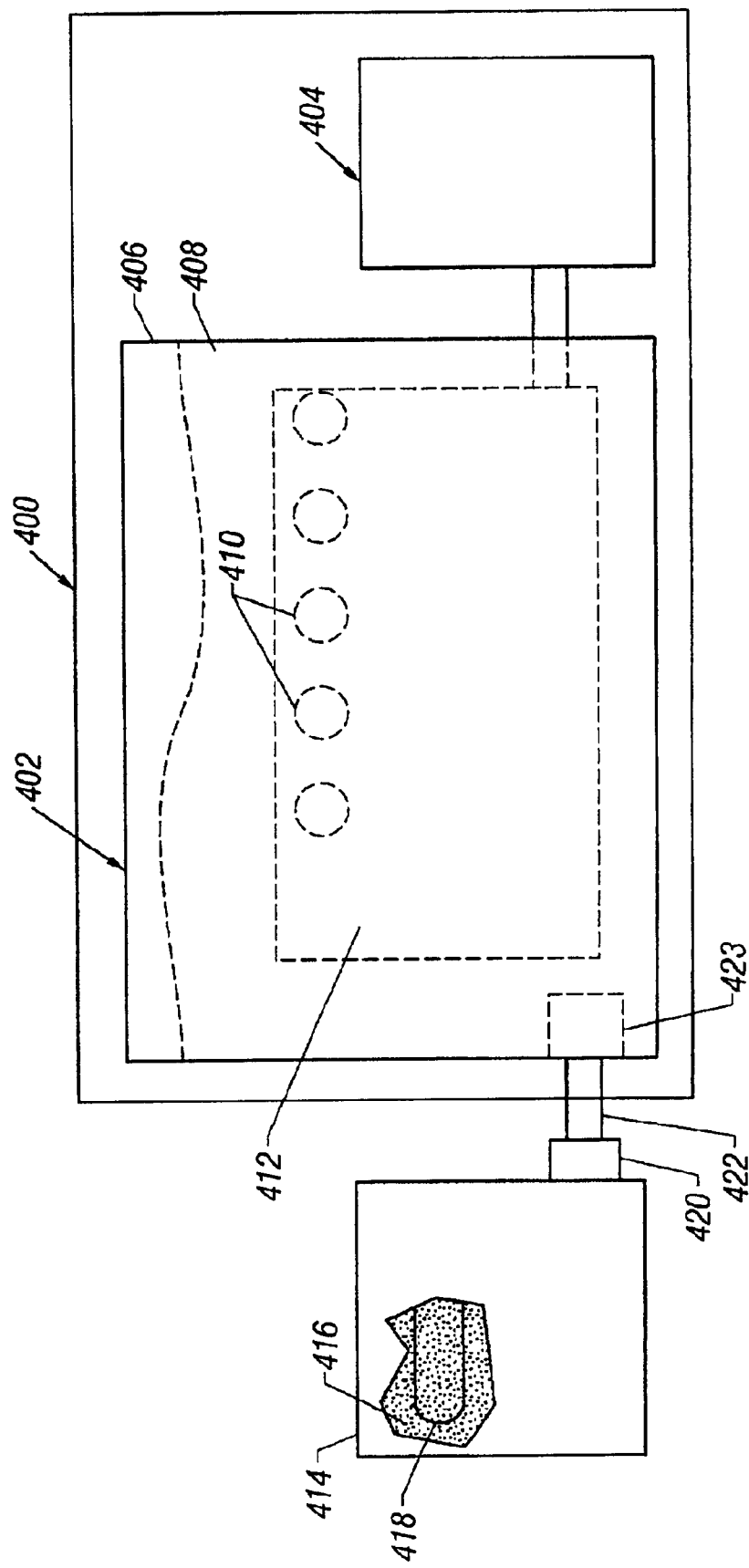
FIG. 17 is a diagrammatic view of a cooling apparatus according to an embodiment of the disclosures herein.

A cooling apparatus 400 capable of cooling articles according to embodiments of the disclosures herein is depicted in FIG. 17. The cooling apparatus 400 includes a cooling unit 402 connected to refrigeration unit 404. The cooling unit 402 preferably includes an insulated tank 406 containing a cooling fluid 408. Submersed in the cooling fluid 408 are a plurality of circulators 410 and a heat exchanging coil 412. A motor having an impeller attached thereto is an example of each one of the circulators 410. The refrigeration unit 404 is external to the insulated tank 406 and is coupled to the heat exchanging coil 412.

In one embodiment of the cooling fluid 408, the cooling fluid 408 is a food grade fluid. Examples of food grade quality cooling fluids are those based on propylene glycol, sodium chloride solutions, or the like.

The insulated tank 406 may be of any dimensions necessary to facilitate cooling of the cooling fluid 408 within the insulated tank 406. In at least one embodiment of the insulated tank 406, the insulated tank 406 is constructed to have a dimension necessary to facilitate super-cooling of the cooling fluid 408 within the insulated tank 406 and to permit one or more objects (e.g. article, biological material, food product, etc.) to be at least partially immersed in the cooling fluid 408.

The insulated container that is disclosed above in reference to FIG. 15 is an example of an object that may be immersed in the cooling fluid 408. Such an insulated container includes a super-coolable composition therein, but does not include a cooling member therein. Accordingly, immersing all or part of the insulated container in the cooling fluid 408 facilitates super-cooling of the super-coolable composition.

The heat exchanging coil 412 is preferably a "multi-path coil," which allows refrigerant from the refrigeration unit 404 to travel through multiple paths (i.e. three or more paths), in contrast to conventional refrigeration coils in which refrigerant is generally restricted to one or two continuous paths. In addition, the coil size is in direct relationship to the cross sectional area containing the measured amount of the cooling fluid 408. For example, in a preferred embodiment, the tank 406 is one foot long, two feet deep and four feet wide, and uses a heat exchanging coil 412 that is one foot by two feet. If the length of the tank 406 is increased to twenty feet, then the length of the heat exchanging coil 412 is also increased to twenty feet. As a result, the heat exchanging coil 412 can be made approximately fifty percent of the size of a conventional coil required to handle the same heat load.

The circulators 410 facilitate flow of the cooling fluid 408 through the tank and over an object (e.g. article, biological material, food product, etc.) if such an object is immersed in the cooling fluid 408, and then direct the cooling fluid 408 into the heat exchanging coil 412. In at least one embodiment, heat exchanging coil 412 is so designed to remove not less than the same amount of heat from cooling fluid 408 as that is removed from an object being cooled, thereby maintaining the temperature of cooling fluid 408 in a predetermined range. The heat exchanging coil 412 is connected to the refrigeration unit 404.

In a preferred embodiment, the refrigeration unit 404 is designed to match the load requirement of the heat exchanging coil 412. Accordingly, heat is removed from the cooling fluid 408 in a balanced and efficient manner, resulting in the controlled, rapid freezing of a composition or object. The efficiency of the refrigeration unit 404 is directly related to the method employed for controlling suction pressures by the efficient feeding of the heat exchange coil 412 and the efficient output of compressors used in refrigeration unit 404.

This methodology of matching load requirements requires relatively close tolerances to be maintained between the temperatures of the refrigerant and the cooling fluid 408, and between the condensing temperature and the ambient temperature. These temperature criteria, together with the design of the heat exchange coil 120, allow the heat exchange coil 412 to be fed more efficiently. In turn, this allows the compressor to be fed in a balanced and tightly controlled manner to achieve in excess of twenty-five percent greater performance from the compressors than that which is accepted as the compressor manufacturer's standard rating.

Note that in the embodiment illustrated in FIG. 17, the refrigeration unit 404 is an external, remotely located refrigeration system. However, in another embodiment (not illustrated), the refrigeration unit 404 is incorporated into another section of the tank 406. It will be appreciated that various configurations for the refrigeration unit 404 may be more or less appropriate for certain configurations of the cooling unit 402. For example, if the tank 406 is extremely large, a separate refrigeration unit 404 may be desirable, while a portable embodiment may benefit from an integrated refrigeration unit 404. Such an integration is only made possible by the efficiencies achieved by implementing the principles as set forth herein, and particularly the use of a reduced-size heat exchanging coil.

By virtue of the refrigeration unit 404 and the heat exchanging coil 412, in a preferred embodiment, the cooling fluid 408 is cooled to a temperature of between −20 degrees Celsius and −30 degrees Celsius, with a temperature differential throughout the cooling fluid of less than about +/−0.5 degrees Celsius. In other embodiments, the cooling fluid 408 is cooled to temperatures outside the −20 degree Celsius to −30 degree Celsius range in order to control the rate at which an object or composition is to be frozen. Other embodiments control the circulation rate of the cooling fluid 408 to achieve desired freezing rates. Alternatively, the volume of the cooling fluid 408 may be changed in order to facilitate a particular freezing rate. It will be appreciated that various combinations of cooling fluid circulation rate, cooling fluid volume, and cooling fluid temperature can be used to achieve desired freezing rates.

As depicted in FIG. 17, an article 414 including a super-coolable composition 416 therein and a cooling member 418 disposed within such super-coolable composition 416 is capable of being attached to the cooling unit 402. The insulated containers disclosed above as having a cooling member therein and the thermal block disclosed above are examples of the article 414. The cooling member 418 includes a coupling means 420 capable of being attached to a cooling fluid conduit 422 of the cooling unit 402. The cooling conduit is configured for enabling the flow of the cooling fluid 408 to and from the cooling unit 402 with respect to the article 414.

Cooling member couplings as disclosed above are examples of the coupling means 420. In operation, when the cooling fluid conduit 422 is attached to the coupling means 420, the cooling fluid 408 is capable of being circulated from by a pump 423 of the cooling unit 402 through the cooling member 418 of the article 414 and back to the cooling unit 402. In this manner, the super-coolable composition 416 of the article 414 is capable of being super-cooled by the cooling apparatus 400.

Preferably, each circulator 410 includes a motors that is capable of being controlled to maintain a constant predetermined velocity of cooling fluid flow past an object while at the same time maintaining an even distribution of cooling fluid temperature within +/−0.5 degrees Celsius at all points within tank 406. The substantially constant predetermined velocity of cooling fluid circulating past the biological material, provides a constant, measured removal of heat, which allows for the vitrification of the water containing compositions and materials during freezing. In one embodiment, cooling fluid properties, such as viscosity, temperature, etc., are measured and processed, and control signals are sent to the motor of one or more of the circulators 410 to increase or decrease the rotational speed or torque of a circulator impeller, as needed. In other embodiments, the impellers of one or more of the circulators 410 are constructed to maintain a given rotational velocity over a range of fluid conditions. In such a case, the torque or rotational speed of an impeller of each circulator 410, as imparted by the attached motor, is not externally controlled. Of note is the fact that no external pumps, shafts, or pulleys are needed to implement a preferred embodiment of the disclosures herein. The motor of each one of the circulators 410 is immersed directly in the cooling fluid 408. As a result, the cooling fluid 408 provides cooling for such motors.

A method 500 according to one embodiment of the disclosures herein is depicted in FIG. 16. The method 500 enables cost efficiencies and freezing speeds that are superior to cost efficiencies and freezing speeds capable with conventional freezing techniques such as blast freezing. The method is capable of being facilitated via a suitable cooling apparatus. The cooling apparatus 400 disclosed above is an example of such a suitable cooling apparatus.

In the method 500, an operation 510 is performed for circulating a cooling fluid in a tank of the cooling apparatus past a heat exchange coil of the cooling apparatus. The heat exchange coil is operably coupled to a refrigeration system as discussed above, and is used to reduce the temperature of the cooling fluid as the cooling fluid is circulated past the heat exchange coil. In response to circulating the cooling fluid past the heat exchanging coil, an operation 520 is performed for determining the temperature of the cooling fluid in the tank. After determining the temperature of the cooling fluid, an operation 530 is performed for determining whether the temperature of the cooling fluid is within a preferred temperature range. This preferred cooling fluid temperature range may be different for different applications, however, a preferred temperature range for many applications is between −20 degrees Celsius and −30 degrees Celsius.

If the cooling fluid temperature is determined not to be within the preferred predetermined temperature range, an operation 535 is performed for adjusting the temperature of the heat exchanging coil. At least one embodiment of the operation 735 includes automatically adjusting the temperature of the heat exchanging coil. The temperature of the heat exchanging coil is capable of being adjusted via a refrigeration unit of the cooling apparatus. Increasing or decreasing the heat transfer level of the heat exchanging coil is one example of a technique adjusting the temperature of the heat exchanging coil. After performing the operation 535 for adjusting the temperature of the heat exchanging coil, the method proceeds to the operation 510 for circulating the cooling fluid past the heat exchanging coil in order to lower the temperature of the cooling fluid. Preferably, the operations 510, 520, 530 and 535 are performed continually until the cooling fluid temperature is in the preferred temperature range.

While the cooling fluid is being cooled to the proper temperature, an operation 540 is performed for attaching a cooling cool of an article to a cooling unit of the cooling apparatus. The insulated containers disclosed above as having a cooling member therein and the thermal blocks disclosed above are examples of such an article. Also as disclosed above, the cooling member is connected to the cooling unit in a manner for permitting the cooling fluid to be circulated to the cooling member from the cooling unit and back to the cooling unit from the cooling member.

After the cooling fluid temperature is determined to be within the preferred temperature range, an operation 545 is performed for initiating the flow of the cooling fluid through the cooling member of the article. As the cooling fluid passes through the cooling member, heat is removed from a super-coolable composition, such as the super-coolable composition disclosed above in reference to FIG. 16. Initially, the super-coolable material is at a higher temperature than the temperature of the cooling fluid. Thus, heat is transferred to the cooling fluid and is transported away from the article via circulation of the cooling fluid through the cooling member. According to at least one embodiment of the present invention, a substantially constant circulation of cooling fluid through the cooling member should be maintained in order to sufficiently cool the super-coolable composition.

In response to initiating the circulation of cooling fluid through the cooling member of the article, an operation 550 is performed for adjusting the velocity at which the cooling fluid is circulated through the cooling member of the article and/or through the circulators as necessary to account for changes in the cooling fluid viscosity, temperature, and the like. Preferably, the velocity at which the cooling fluid is circulated through the cooling member of the article and through the circulators is held constant by adjusting a respective force provided by a pump that controls the circulation of the cooling fluid through the cooling member and a motor attached to each circulator.

Figure 18:
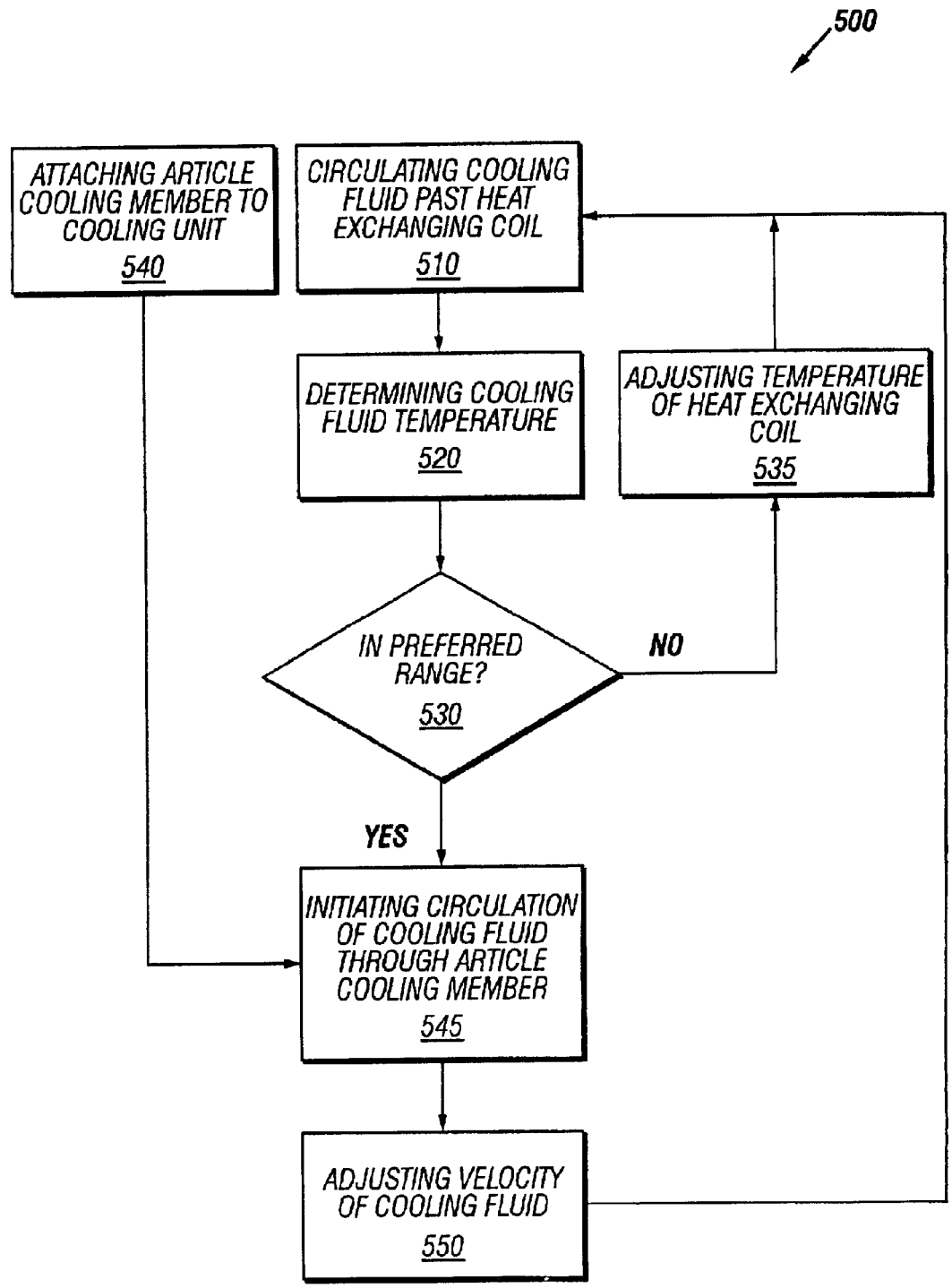
FIG. 18 is a flow diagram view of a process according to an embodiment of the disclosures herein capable of cooling an article according to an embodiment of the disclosures herein.

The operations illustrated in FIG. 18 are shown and discussed in a sequential order. However, the illustrated method is of a nature wherein some or all of the steps are continuously performed, and may be performed in a different order. In one embodiment of the present invention measures cooling fluid temperatures, viscosity and other fluid properties continually, and at multiple locations within the system. In another embodiment, some properties of the cooling fluid are not directly measured. Rather, the change in cooling fluid properties is determined indirectly from the rotational speed of a motor connected to the pump or from the rotational speed motors attached to respective cooling fluid circulators of the cooling unit. If the a motor is turning at a slower rate that a prescribed rate, then additional power can be supplied to such motor to return the motor to a desired rotational speed, thereby compensating for the change in cooling fluid properties. In at least one embodiment, motor attached to pumps and circulators of the cooling unit are configured to maintain a substantially constant rate of rotation. This substantially constant rate of motor rotation will result in a substantially constant rate of cooling fluid circulation.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. An organ preservation system, comprising:
a perfusion liquid delivery apparatus;
a perfusion liquid pumping apparatus connected to the perfusion liquid delivery apparatus and capable of delivering a perfusion liquid to the perfusion liquid delivery apparatus;
a thermal mass including a thermal mass cooling core body having a core cavity therein, including a cooling member disposed in the core cavity of the thermal mass cooling core body, and including a coolable composition disposed within the core cavity of the thermal mass cooling core body encapsulating at least a portion of the cooling member; and
a system container including a system container cooling core body having a core cavity therein and a coolable composition disposed within the core cavity of the system container cooling core body, wherein the system container includes a container cavity therein capable of receiving the perfusion liquid delivery apparatus, the perfusion liquid pumping apparatus, and the thermal mass disposed therein;
wherein the cooling member of the thermal mass cooling core body is connected between the perfusion liquid delivery apparatus and the perfusion liquid pumping apparatus and is capable of having the perfusion liquid routed therethrough for enabling the perfusion liquid to be cooled.

2. The organ preservation system of claim 1 wherein:
the system container further includes a cooling member disposed in the core cavity of the system container cooling core body; and
the coolable composition of the system container encapsulates at least a portion of the cooling member of the system container.

3. The organ preservation system of claim 3 wherein:
the system container cooling core body includes a first cooling core shell and a second cooling core shell attached to the first cooling core shell; and
the core cavity of the system container cooling core body is defined between the first cooling core shell and the second cooling core shell.

4. The organ preservation system of claim 2 wherein the cooling member of the system container includes a plurality of cooling member segments.

5. The organ preservation system of claim 2 wherein the cooling member of the system container is a multi-pass cooling member.

6. The organ preservation system of claim 2 wherein:
the cooling member of the system container includes a first cooling member coupling and a second cooling member coupling; and
the first cooling member coupling and the second cooling member coupling are each detachably connectable to a cooling apparatus for enabling a super-cooled cooling fluid to be circulated therethrough for super-cooling the coolable composition of the system container.

7. The organ preservation system of claim 1 wherein the system container further includes an insulating shell having the system container cooling core body disposed therein.

8. The organ preservation system of claim 1 wherein the system container further includes an insulating insert disposed within the core cavity of system container cooling core body.

9. The organ preservation system of claim 8 wherein:
the system container cooling core body includes a first cooling core shell and a second cooling core shell attached to the first cooling core shell; and
the core cavity of the system container cooling core body is defined between the first cooling core shell and the insulating shell.

10. The organ preservation system of claim 9 wherein the system container further includes a cooling member disposed within the core cavity of the system container cooling core body essentially encapsulated within the coolable composition of the system container.

11. The organ preservation system of claim 1, wherein the coolable composition of the system container and the coolable composition of the thermal mass are each made by a process comprising:
   forming a first mixture including water and ethanol, wherein the first mixture has a first pH level;
   adjusting the pH level of the first mixture to have a second pH level different than the first pH level; and
   combining a water-soluble binding agent with the first mixture to form a second mixture.

12. An organ preservation system, comprising:
   a perfusion liquid delivery apparatus;
   a perfusion liquid pumping apparatus connected to the perfusion liquid delivery apparatus and capable of delivering a perfusion liquid to the perfusion liquid delivery apparatus;
   a thermal mass including a thermal mass cooling core body having a core cavity therein, including a cooling member disposed in the core cavity of the thermal mass cooling core body, and including a coolable composition disposed within the core cavity of the thermal mass cooling core body encapsulating at least a portion of the cooling member;
   wherein the cooling member of the thermal mass cooling core body is connected between the perfusion liquid delivery apparatus and the perfusion liquid pumping apparatus and is capable of having the perfusion liquid routed therethrough for enabling the perfusion liquid to be cooled;
   wherein the perfusion liquid delivery apparatus includes an organ container, the organ container capable of having an organ disposed therein immersed in a bath of the perfusion liquid; and
   wherein the organ container includes an organ container cooling core body having a core cavity therein and a coolable composition disposed within the core cavity of the organ container cooling core body.

13. The organ preservation system of claim 12 wherein:
   the organ container further includes a cooling member disposed in the core cavity of the organ container cooling core body; and
   the coolable composition of the organ container encapsulates at least a portion of the cooling member of the organ container.

14. The organ preservation system of claim 13 wherein:
   the organ container cooling core body includes a first cooling core shell and a second cooling core shell attached to the first cooling core shell; and
   the core cavity of the organ container cooling core body is defined between the first cooling core shell and the second cooling core shell.

15. The organ preservation system of claim 13 wherein the cooling member of the organ container includes a plurality of cooling member segments.

16. The organ preservation system of claim 13 wherein the cooling member of the organ container is a multi-pass cooling member.

17. The organ preservation system of claim 13 wherein:
   the cooling member of the organ container includes a first cooling member coupling and a second cooling member coupling; and
   the first cooling member coupling and the second cooling member coupling are each detachably connectable to a cooling apparatus for enabling a super-cooled cooling fluid to be circulated therethrough for super-cooling the coolable composition of the organ container.

18. The organ preservation system of claim 12 wherein the organ container further includes an insulating shell having the organ container cooling core body disposed therein.

19. The organ preservation system of claim 12 wherein the organ container further includes an insulating insert disposed within core cavity of the organ container cooling core body.

20. The organ preservation system of claim 19 wherein:
   the organ container cooling core body includes a first cooling core shell and a second cooling core shell attached to the first cooling core shell; and
   the core cavity of the organ container cooling core body is defined between the first cooling core shell and the insulating shell.

21. The organ preservation system of claim 20 wherein the organ container further includes a cooling member disposed within the core cavity of the organ container cooling core body essentially encapsulated within the coolable composition of the organ container.

22. The organ preservation system of claim 12 wherein the coolable composition of the organ container cooling core body and the coolable composition of the thermal mass cooling core body are each made by a process comprising:
   forming a first mixture including water and ethanol, wherein the first mixture has a first pH level;
   adjusting the pH level of the first mixture to have a second pH level different than the first pH level; and
   combining a water-soluble binding agent with the first mixture to form a second mixture.

23. An organ preservation system, comprising:
   an organ container;
   a perfusion liquid delivery apparatus;
   a perfusion liquid pumping apparatus connected to the perfusion liquid delivery apparatus and capable of delivering a perfusion liquid to the perfusion liquid delivery apparatus;
   a thermal mass including a thermal mass cooling core body having a core cavity therein, including a cooling member disposed in the core cavity of the thermal mass cooling core body and having a first cooling member coupling and a second cooling member coupling, and including a coolable composition disposed within the core cavity of the thermal mass cooling core body encapsulating at least a portion of the cooling member; and
   a system container including a container cavity therein capable of receiving the perfusion liquid delivery apparatus, the perfusion liquid pumping apparatus, the organ container and the thermal mass therein, the system container including a system container cooling core body having a core cavity therein, including a cooling member disposed in the core cavity of the system container cooling core body and including a first cooling member coupling and a second cooling member coupling, and including a coolable composition disposed within the core cavity of the system container cooling core body encapsulating at least partially encapsulating the cooling member;
   wherein:
   the cooling member of the thermal mass cooling core body is coupled between the perfusion liquid delivery apparatus and the perfusion liquid pumping apparatus and is capable of having the perfusion liquid routed therethrough for enabling the perfusion liquid to be cooled;

the organ container is capable of having an organ disposed therein immersed in a bath of the perfusion liquid;

the first cooling member coupling and the second cooling member coupling of both the thermal mass and the system container are each detachably connected to a respective perfusion liquid conduit for enabling the perfusion liquid to be routed therethrough; and the first cooling member coupling and the second cooling member coupling of both the thermal mass and the system container are each detachably connectable to a cooling apparatus for enabling a super-cooled cooling fluid to be circulated therethrough for super-cooling the coolable composition of the thermal mass.

\* \* \* \* \*